US011597740B2

(12) United States Patent
Jennewein

(10) Patent No.: US 11,597,740 B2
(45) Date of Patent: *Mar. 7, 2023

(54) PROCESS FOR EFFICIENT PURIFICATION OF NEUTRAL HUMAN MILK OLIGOSACCHARIDES (HMOS) FROM MICROBIAL FERMENTATION

(71) Applicant: Chr. Hansen HMO GmbH, Rheinbreitbach (DE)

(72) Inventor: Stefan Jennewein, Bad Honnef (DE)

(73) Assignee: Chr. Hansen HMO GmbH, Rheinbreitbach (DE)

( * ) Notice: Subject to any disclaimer, the term of this patent is extended or adjusted under 35 U.S.C. 154(b) by 0 days.

This patent is subject to a terminal disclaimer.

(21) Appl. No.: 17/097,488

(22) Filed: Nov. 13, 2020

(65) Prior Publication Data

US 2021/0061836 A1    Mar. 4, 2021

Related U.S. Application Data

(60) Division of application No. 16/277,731, filed on Feb. 15, 2019, now Pat. No. 10,882,880, which is a continuation of application No. 15/112,724, filed as application No. PCT/EP2014/079212 on Dec. 23, 2014, now Pat. No. 10,377,787.

(30) Foreign Application Priority Data

Jan. 20, 2014   (EP) .................................... 14151737

(51) Int. Cl.
| C07H 1/08 | (2006.01) |
| A23L 5/00 | (2016.01) |
| C07H 3/06 | (2006.01) |
| A23L 29/30 | (2016.01) |
| A23L 33/00 | (2016.01) |
| A23L 33/21 | (2016.01) |
| A61K 31/702 | (2006.01) |
| C12P 19/14 | (2006.01) |

(52) U.S. Cl.
CPC .................. *C07H 1/08* (2013.01); *A23L 5/00* (2016.08); *A23L 29/30* (2016.08); *A23L 33/21* (2016.08); *A23L 33/40* (2016.08); *A61K 31/702* (2013.01); *C07H 3/06* (2013.01); *C12P 19/14* (2013.01); *A23V 2002/00* (2013.01)

(58) Field of Classification Search
None
See application file for complete search history.

(56) References Cited

U.S. PATENT DOCUMENTS

| 5,945,314 A | 8/1999 | Prieto et al. |
| 6,017,433 A | 1/2000 | Mani |
| 6,280,985 B1 | 8/2001 | Caboche et al. |
| 6,454,946 B1 | 9/2002 | Defrees |
| 6,706,497 B2 | 3/2004 | Pelletier et al. |
| 7,521,212 B1 | 4/2009 | Samain et al. |
| 9,283,240 B2 | 3/2016 | Buck et al. |
| 9,611,285 B2 | 4/2017 | Parkot et al. |
| 10,377,787 B2 * | 8/2019 | Jennewein .............. A23L 29/30 |
| 10,882,880 B2 | 1/2021 | Jennewein |
| 2007/0274955 A1 | 11/2007 | Gibson et al. |
| 2008/0145899 A1 | 6/2008 | Johnson et al. |
| 2010/0143535 A1 | 6/2010 | Motoshima et al. |
| 2010/0248315 A1 | 9/2010 | Beuzelin-Ollivier et al. |
| 2011/0177044 A1 | 7/2011 | Thomas et al. |
| 2011/0300584 A1 | 12/2011 | Huefner et al. |
| 2012/0121788 A1 | 5/2012 | Scott et al. |
| 2012/0171165 A1 | 7/2012 | Buck et al. |
| 2012/0294840 A1 | 11/2012 | Newburg et al. |
| 2013/0217068 A1 | 8/2013 | Parkot et al. |
| 2016/0186223 A1 | 6/2016 | Jennewein |
| 2016/0237104 A1 | 8/2016 | Jennewein |
| 2016/0333042 A1 | 11/2016 | Jennewein |

(Continued)

FOREIGN PATENT DOCUMENTS

| CN | 102154163 A | 8/2011 |
| CN | 101691538 B | 5/2012 |

(Continued)

OTHER PUBLICATIONS

Notice of opposition (FrieslandCampina Nederland B.V.) to European Patent No. 2896628 dated Jun. 12, 2019.

(Continued)

*Primary Examiner* — Christian L Fronda
(74) *Attorney, Agent, or Firm* — McNeill Baur PLLC

(57) ABSTRACT

The present application discloses a simple process for the purification of neutral human milk oligosaccharides (HMOs) produced by microbial fermentation. The process uses a combination of cationic ion exchanger treatment, an anionic ion exchanger treatment, and a nanofiltration and/or electrodialysis step, which allows efficient purification of large quantities of neutral HMOs at high purity. Contrary to the purification currently used in fermentative production of neutral HMOs, the presented process allows the provision of HMOs without the need of a chromatographic separation. The so purified HMOs may be obtained in solid form by spray drying, as crystalline material or as sterile filtered concentrate. The provided HMOs are free of proteins and recombinant material originating from the used recombinant microbial strains and thus very well-suited for use in food, medical food and feed (e.g. pet food) applications.

5 Claims, 3 Drawing Sheets

(56) References Cited

U.S. PATENT DOCUMENTS

| | | |
|---|---|---|
| 2017/0044538 A1 | 2/2017 | Rigo et al. |
| 2019/0292211 A1 | 9/2019 | Jennewein et al. |

FOREIGN PATENT DOCUMENTS

| | | |
|---|---|---|
| CN | 103468766 A | 12/2013 |
| EP | 2013367 B1 | 3/2011 |
| EP | 2479263 A1 | 7/2012 |
| EP | 2526784 A1 | 11/2012 |
| EP | 2722394 A1 | 4/2014 |
| EP | 2845905 A1 | 3/2015 |
| EP | 2857410 A1 | 4/2015 |
| EP | 2896628 A1 | 7/2015 |
| EP | 2379708 B1 | 4/2016 |
| EP | 3063159 A1 | 9/2016 |
| EP | 3131912 A1 | 2/2017 |
| EP | 3131915 A2 | 2/2017 |
| EP | 3375786 A1 | 9/2018 |
| JP | S61-271296 A | 12/1986 |
| JP | 63273491 A | 11/1988 |
| JP | 2001514865 A | 9/2001 |
| JP | 2001518783 A | 10/2001 |
| JP | 2003047402 A | 2/2003 |
| JP | 2003048901 A | 2/2003 |
| JP | 2012520666 A | 9/2012 |
| JP | 2012522827 A | 9/2012 |
| JP | 2013121343 A | 6/2013 |
| JP | 2013541952 A | 11/2013 |
| RU | 2313572 C2 | 12/2007 |
| TW | 201233334 A | 8/2012 |
| TW | 201233340 A | 8/2012 |
| WO | 2004101479 A2 | 11/2004 |
| WO | 2006038552 A1 | 4/2006 |
| WO | 2007130247 A1 | 11/2007 |
| WO | 2009008362 A1 | 1/2009 |
| WO | 2010/115935 A1 | 10/2010 |
| WO | 2010142305 A1 | 12/2010 |
| WO | 2011005681 A1 | 1/2011 |
| WO | 2011150939 A1 | 12/2011 |
| WO | 2012/069415 A1 | 5/2012 |
| WO | 2012/092160 A2 | 7/2012 |
| WO | 2012097950 A1 | 7/2012 |
| WO | 2012/112777 A2 | 8/2012 |
| WO | 2012/160080 A1 | 11/2012 |
| WO | 2012158517 A1 | 11/2012 |
| WO | 2013/025104 A1 | 2/2013 |
| WO | 2013096420 A1 | 6/2013 |
| WO | 2013/182206 A1 | 12/2013 |
| WO | 2013185780 A1 | 12/2013 |
| WO | 2014009921 A2 | 1/2014 |
| WO | 2014018596 A2 | 1/2014 |
| WO | 2014086373 A1 | 6/2014 |
| WO | 2015049331 A1 | 4/2015 |
| WO | 2015/106943 A1 | 7/2015 |

OTHER PUBLICATIONS

Notice of opposition (Strawman Limited) to European Patent No. 2896628 dated Jun. 18, 2019.
Notice of opposition (BASF SE) to European Patent No. 2896628 dated Jun. 19, 2019.
Notice of opposition (Glycom A/S) to European Patent No. 2896628 dated Jun. 19, 2019.
Notice of opposition (Greaves-Brewster) to European Patent No. 2896628 dated Jun. 18, 2019.
Yu, Zhuo-Teng et al., "The principal fucosylated oligosaccharides of human milk exhibit prebiotic properties on cultured infant microbiota", Glycobiology, 2013, pp. 169-177, vol. 23, No. 2.
Braithwaite, A. et al., "Chromatographic Methods", London: Chapman and Hall Ltd, 1985, Ed. 4th ISBN: 9789401083164, relevant pp. 1-7.
"WHO Expert Committee on Specifications for Pharmaceutical Preparations—WHO Technical Report Series, No. 885—Thirty-fifth Report", [cited Sep. 5, 2019] Available from: [apps.who.int/medicinedocs/en/p/printable.html].
Patentee submission during Examination of the patent in suit, Jul. 7, 2017.
Patentee submission during Examination of the patent in suit, Oct. 10, 2016.
Patentee submission during Examination of the patent in suit, Mar. 21, 2018.
Wang, Qiushuang et al., "Demineralization of soybean oligosaccharides extract from sweet slurry by conventional electrodialysis", Journal of Food Engineering, 2009, pp. 410-415, vol. 95.
Minutes from oral proceedings on Jun. 4, 2018 (in EP2896628).
Mcmurry, John: Organic Chemistry, 6th Ed. (2004), 415-416.
Seader, JD et al., Separation Process Principles (Chemical and Biochemical Operations) 3rd Ed (2010): 577-578.
Buttler, Torbjorn et al., "Characterization of a sampling unit based on tangential flow filtration for on-line bioprocess monitoring", Analytica Chimica Acta, 1993, pp. 27-37, vol. 279.
Ezure, Yohji, "Manufacturing High Purity Maltose and Maltotetraose from Starch by a Novel and Efficient Procedure Named 'Reducing End Modification Method'", Biosci. Biotech. Biochem., 1997, pp. 1931-1933, vol. 61, No. 11.
Wikipedia article "Electrodialysis" version of Jan. 6, 2014.
Drouillard, Sophie et al., "Large-Scale Synthesis of H-Antigen Oligosaccharides by Expressing Helicobacter pylori [alpha]1,2-Fucosyltransferase in Metabolically Engineered *Escherichia coli* Cells.", Angew. Chem. Int. Ed., Feb. 2006, pp. 1778-1780, vol. 45.
Arteagua-Cabello, Fernando et al., "Synthesis of 2-FL and LDFT by metabolically engineered *E. coli* through the fkp gene from Bacteroides fragilis"; Annual conference of the Society for Glycobiology, Nov. 2011, p. 1499.
Dekker, Marcel, "Preparative and Production Scale Chromatography", Chromatographic Science Series, 1993, pp. 617-620, (Levinson) New York.
Applicant's letter dated Oct. 10, 2016 (EP2896628).
GRAS Notification for 2'-Fucosyllactose (2'-FL), extract from GRN 571.
Appendix K, Description and Safety Evaluation of *E. coli* BL21 #1540, from GRN 571 (GRAS Notice).
FDA, GRAS Notices, GRN No. 571 (1 page).
Stock, R. et al., "Chromatographic Methods", 1974, pp. 1-51, 3rd Edition, New York, John Wiley & Sons.
Farrell, Stephanie et al., "Exploring the Potential of Electrodialysis", Chemical Engineering Education, Dec. 2003, pp. 52-59, vol. 37.
Datasheet for Lewatit S 6368 (Lanxess, 2011).
Datasheet for Lewatit S 2568 (Lanxess, 2009).
Structural similarities of neutral HMOs.
Wikipedia article "Chromatography", last edited Jun. 10, 2019.
Stanbury, Peter F., Chapter 1: Fermentation Technology: in Walker JM, Rapley R (eds.) Molecular Biology and Biotechnology. Royal Soc. of Chemistry. 1-24.
Third Party Observation for application No. EP 20180169031 dated May 31, 2019.
Summary of purification protocols described in Examples 1 and 2 of EP 2896628 B1.
Austrian Search Report for Application No. 50165/2019 dated Feb. 17, 2021.
Second Office Action of Russian Patent Application No. 2016128955 dated Oct. 1, 2018.
IP Australia, Examination Report No. 1 in Australian Patent Application No. 2014377374 (dated Jun. 26, 2018).
State Intellectual Property Office of the People's Republic of China, First Office Action in Chinese Patent Application No. 201480073484.0 (dated Jun. 15, 2018).
European Patent Office, Communication pursuant to Article 94(3) EPC in European Application No. 14827224.8 (dated May 8, 2018).
Bao et al., "Quantification of neutral human milk oligosaccharides by graphitic carbon HPLC with tandem mass spectrometry," Anal Biochem 433(1): 28-35 (2013).
Boehm et al., "Oligosaccharides from Milk," J. Nutr 137(3 Suppl 2): 847S-849S (2007).

(56) References Cited

OTHER PUBLICATIONS

Sumiyoshi et al., "Determination of each neutral oligosaccharide in the milk of Japanese women during the course of lactation," Br. J Nutr 89: 61-69 (2003).
Urashima et al., "The Predominance of Type I Oligosaccharides Is a Feature Specific to Human Breast Milk," Adv Nutr 3: 473S-482S (2012).
Saufi et al. J Chromatogr A. Dec. 16, 2011; 1218(50):9003-9.
Sarney et al. Biotechnol Bioeng. Aug. 20, 2000; 69(4):461-7.
European Patent Office, Search Report issued in European Application No. 14151737.5 (dated Mar. 10, 2017).
European Patent Office, Communication under Article 94(3) in European Application No. 14827224.8 (dated Jun. 6, 2017).
Albermann et al., "Synthesis of the milk oligosaccharide 2'-fucosyllactose using recombinant bacterial enzymes," Carbohydr. Res. 334(2): 97-103 (2001).
Baumgaertner et al., Construction of *Escherichia coli* strains with chromosomally integrated expression cassettes for the synthesis of 2'-fucosyllactose, Microb. Cell Fact. 12:40 (2013)—13 pgs.
Bode et al., "Structure-Function Relationships of Human Milk Oligosaccharides," Adv. Nutr. 3: 383S-391S (2012).
Bode, "Human milk oligosaccharides: every baby needs a sugar mama," Glycobiology 22(9): 1147-1162 (2012).
Castanys-Munoz et al., "2'-fucosyllactose: an abundant, genetically determined soluble glycan present in human milk," Nutr. Rev. 71(12): 773-789 (2013).
Gura, "Nature's First Functional Food," Science 345(6198): 747-749 (2014).
Lee et al., "Whole cell biosynthesis of a functional oligosaccharide, 2'-fucosyllactose, using engineered *Escherichia coli*," Microb. Cell Fact. 11:48 (2012) (9pgs.).
Morrow et al., "Human Milk Oligosaccharides are Associated With Protection Against Diarrhea in Breast-Fed Infants," J. Pediatrics 145(3): 297-303 (2004).
Sarney et al., "A novel approach to the recovery of biologically active oligosaccharides from milk using a combination of enzymatic treatment and nanofiltration," Biotechnol. Bioeng 69: 461-467 (2000).
European Patent Office, International Search Report in International Application No. PCT/EP2014/079212 (dated Jun. 18, 2015).
European Patent Office, Written Opinion in International Application No. PCT/EP2014/079212 (dated Jun. 18, 2015).
International Bureau of WIPO, International Preliminary Report on Patentability in International Application No. PCT/EP2014/079212 (dated Aug. 4, 2016).
Miyazaki et al., "Enzymatic synthesis of lacto-N-difucohexaose I which binds to Helicobacter pylori," Methods in Enzymology 480: 511-524 (2010).
Murata et al., "Facile enzymatic conversion of lactose into lacto-N-tetraose and lacto-N-neotetraose", Glycoconj. J. 16(3): 189-195 (1999).
Summons to attend Oral Hearings of European Application No. 14827224.8 dated Mar. 14, 2019.
Korean Office Action [English translation] of Korean Patent Application No. 10-2016-7022587 dated Apr. 10, 2019.
Third Party Observation for European Application No. 20140827224.
Office Action in Corresponding Chinese Application No. 20148073484.0 dated Nov. 13, 2019.
Common Knowledge 1: Molecular Biological Testing Technology, Chapter III: Separation and Purification of Biological Macromolecules, edited by Lishe Zhou, 2012, p. 39.
Common Knowledge 2: Production and Analysis Technology of Protein and Nucleic Acid Medicines, 3.1.5. 2 Separation and Purification of Nucleic Acid by Ion Exchange Chromatography, edited by Xiao Tang, 2012, p. 149.
Common Knowledge 3: 100 Experts Talk about Milk: Collection of Scientific Milk Drinking Popularization Projects, edited by Jianping Jiang, Shuyuan Li, 2008, Development and Application of Prebiotics and Breastmilk Dairy Products, pp. 257-259.
Opposition of European Patent EP3131912 dated Jan. 22, 2020.

Salehi, Current and future applications for nanofiltration technology in the food processing; Food and Bioproducts Processing. 2014; 92:161-177.
Nagy, Endre, "Basic Equations of the Mass Transport through a Membrane Layer", Chapter 10, pp. 249-266, Elsevier, 2012, ISBN: 978-0-12-416025-5.
Third Party Observation for application No. EP 20140151737 dated May 11, 2018.
Third Party Observation for application No. EP 20140827224 dated Sep. 10, 2018.
Third Party Observation for application No. EP20180169031 dated Jun. 11, 2018.
Third Party Observation for application No. EP 20140827224 dated Feb. 11, 2018 (41 pages).
Third Party Observation for application No. EP 20140827224 dated Feb. 11, 2018 (7 pages).
Third Party Observation for application No. EP 20140827224 dated Jun. 11, 2018 (5 pages).
Li, Yebo, et al., "Separation of cells and proteins from fermentation broth using ultrafiltration," Journal of food engineering, (2006), vol. 75, No. 4: 574-580.
Dechow, Frederick J, et al. "Ion exchange," Fermentation and Biochemical Engineering Handbook, William Andrew Publishing, (1996) 382-475.
Çelebi, İpek, and N. Suzan Kincal. "Color Formation in Wheat Starch Based Glucose Syrups and Use of Commercially Available and Laboratory-Prepared Agricultural Waste-based Activated Carbons for Decolorization." Separation Science and Technology 42.8 (2007): 1761-1773.
Reply by FrieslandCampina to Statement of Appeal in EP2896628, May 3, 2022, 19 pages.
Reply by Greaves Brewster to Statement of Appeal in EP2896628, May 13, 2022, 16 pages.
Scobell et al., "Rapid High-Resolution Separation of Oligosaccharides on Silver Form Cation-Exchange Resins," J Chromatography, 1981, 212:51-64.
Statement on Grounds for Appeal by Chr. Hansen HMO GmbH in Opposition of EP2896628, dated Dec. 22, 2021, 57 pages.
Statement on Grounds for Appeal by FrieslandCampina in Opposition of EP3131912, dated Nov. 3, 2022, 16 pages.
Statement on Grounds for Appeal by Glycom in Opposition of EP3131912, dated Nov. 18, 2022, 57 pages.
Statement on Grounds for Appeal by Greaves Brewster in Opposition of EP3131912, dated Nov. 17, 2022, 27 pages.
Supplemental Reply by FrieslandCampina to Statement of Appeal in EP2896628, Jul. 13, 2022, 4 pages.
Supplementary Response to Replies to Statement on Grounds for Appeal by Chr. Hansen HMO GmbH in Opposition of EP2896628, dated Nov. 7, 2022, 25 pages.
Tan et al., "DNA, RNA, and Protein Extraction: The Past and the Present," J Biomedicine and Biotechnology, 2009, ID:574398, 10 pages.
The Dupont Separability Advisor: Indexing Chromatographic Separations of Sugars, Sugar Alcohols, and Impurities with DuPont Resins, Aug. 2021, 4 pages.
Urrutia et al., "Detailed analysis of galactooligosaccharides synthesis with beta-galactosidase from Aspergillus oryzae," J Agric Food Chem, 2013, 61(5):1081-7 (abstract only).
Werner, "Purification of Proteins: Converting a Culture Broth into a Medicine," The Clinical Pharmacology of Biotechnology Products, Elsevier Science Publishers B.V., 1991, 20 pages.
Wikipedia article, "Human milk Oligosaccharide," last edited Jan. 3, 2021, 3 pages.
Written Submission from BASF in Opposition of EP2896628, dated May 11, 2021, 6 pages.
Written Submission from BASF in Opposition of EP3131912, dated Feb. 25, 2022, 12 pages.
Written Submission from Chr. Hansen HMO GmbH in Opposition of EP2896628, dated May 12, 2021, 41 pages.
Written Submission from FrieslandCampina in Opposition of EP3131912, dated Feb. 16, 2022, 3 pages.
Written Submission from Glycom in Opposition of EP2896628, dated May 7, 2021, 9 pages.

(56) References Cited

OTHER PUBLICATIONS

Written Submission from Glycom in Opposition of EP2896628, dated Sep. 10, 2020, 24 pages.
Written Submission from Glycom in Opposition of EP3131912, dated Mar. 29, 2022, 4 pages.
Written Submission from Greaves Brewster in Opposition of EP2896628, dated Jun. 25, 2021, 3 pages.
Written Submission from Greaves Brewster in Opposition of EP2896628, dated May 12, 2021, 9 pages.
Written Submission from Greaves Brewster in Opposition of EP3131912, dated Feb. 24, 2022, 19 pages.
Written Submission from Jennewein in Opposition of EP2896628, dated Sep. 18, 2020, 11 pages.
Written Submission from Nestle Deutschland in Opposition of EP2896628, dated Sep. 10, 2020, 28 pages.
Wrzosek et al., "Spray drying of the mixtures of mono-, di-, and oligosaccharides," Acta Chimica Slovaca, 2013, 6(2):177-181.
Experimental Report by Greaves Brewster filed in opposition of EP 3131912, dated Nov. 17, 2022, 2 pages.
Bode et al., "Overcoming the limited availability of human milk oligosaccharides: challenges and opportunities for research and application," Nutrition Review, 2016, 74(10):635-644.
Annex to Communication for Summons to Oral Proceedings in an Opposition received in EP2896628, dated Apr. 22, 2020, 15 pages.
Annex to Communication for Summons to Oral Proceedings in an Opposition received in EP3131912, dated Sep. 20, 2021, 20 pages.
Ausubel et al., Preparation and Analysis of Glycoconjugates, Chapter 17, Current Protocols in Molecular Biology, John Wiley & Sons, 2003, 7 pages.
Bych et al., "Production of HMOs using microbial hosts—from cell engineering to large scale production," Current Opinion in Biotechnology, 2019, 56:130-137.
Commission Implementing Decision 2016/376, authorizing the placing on the market of 2'-O-fucosyllactose as a novel food ingredient, Official Journal of the European Union, Mar. 11, 2016, 5 pages.
Commission Implementing Decision 2017/2201, authorizing the placing on the market of 2'-fucosyllactose produced with *Escherichia coli* strain BL21 as a novel food ingredient, Official Journal of the European Union, Nov. 27, 2017, 5 pages.
Commission Implementing Regulation 2019/388 authorizing the change of the specifications of the novel food 2'-fucosyllactose produced with *Escherichia coli* K-12, Official Journal of the European Union, Mar. 11, 2019, 4 pages.
Comparative Results of 2'FL Preparation, 1 page.
De Dardel et al., Ion Exchangers, Ullmann's Encyclopedia of Industrial Chemistry, John Wiley and Sons, 2002, 75 pages.
Decision in Opposition of EP2896628, dated Aug. 25, 2021, 47 pages.
Decision in Opposition of EP3131912, dated Jul. 8, 2022, 79 pages.
DuPont Technical Manual, Chromatographic Separation of Fructose and Glucose with Amberlite CR99 Ion Exchange Resins, Aug. 2020, 15 pages.
Dupont, Ion Exchange and Adsorbent Solutions for the Nutrition Market, Aug. 2021, 16 pages.
European Food Safety Authority, "Guidance on the risk assessment of genetically modified microorganisms and their products intended for food and feed use," EFSA Journal, 2011, 9(6):2193, 54 pages.
European Food Safety Authority, "Safety of 2'-O-fucosyllactose as a novel food ingredient pursuant to Regulation (EC) No. 258/97," EFSA Journal, 2015, 13(7):4184, 32 pages.
Expert Declaration by Dr. Hans van den Brink, Dec. 21, 2021, 6 pages.
Expert Declaration by Karen Pardoe, Dec. 21, 2021, 4 pages.
Expert Declaration by Prof. Dr. Helmut Ritter, Dec. 22, 2021, 5 pages.
Expert Statement by Stefan Jennewein, Dec. 30, 2019, 4 pages.
File History of EP 2,896,628, filed Jan. 20, 2014, Inventor: Stefan Jennewein, 7664 pages.
File History of EP 3,131,912, filed Dec. 23, 2014, Inventor: Stefan Jennewein, 6036 pages.
FriedslandCampina's Reply to Proprietor's Response to the Notices of Opposition in EP3131912, dated Jan. 30, 2020, 3 pages.
Fulmer et al., "NMR Chemical Shifts of Trace Impurities: Common Laboratory Solvents, Organics, and Gases in Deuterated Solvents Relevant to the Organometallic Chemist," Organometallics, 2010, 29:2176-2179.
Linhardt et al., Separation and Purification of Carbohydrates, Chapter 1.3, Glycoscience: Chemistry and Biology I-III, 2001, 63-74.
Machine Translation of CN103468766, dated Dec. 25, 2013, 19 pages.
Machine translation of JP2003-048901, Izumi et al., Feb. 21, 2003, 12 pages.
Mitsubishi Chemical DIAION Technical Guide, "Ion Exchange Resin for Sugar Chromatography," 2020, 4 pages.
Muzaffar et al., "Stickiness Problem Associated with Spray Drying of Sugar and Acid Rich Foods: A Mini Review," J Nutr Food Sci, 2015, S12, 3 pages.
Notice of Appeal from Chr. Hansen HMO GmbH of Opposition decision for EP2896628, dated Oct. 22, 2021, 1 page.
Notice of Appeal from FrieslandCampina of Opposition decision for EP3131912, dated Sep. 2, 2022, 1 page.
Notice of Appeal from Glycom of Opposition decision for EP3131912, dated Sep. 5, 2022, 1 page.
Notice of Appeal from Greaves Brewster of Opposition decision for EP3131912, dated Sep. 8, 2022, 1 page.
Notice of Intervention in Opposition in EP2896628 by Nestle Deutschland, dated Apr. 23, 2020, 67 pages.
Notice of Opposition (BASF) to European Patent No. 3131912, dated Oct. 22, 2020.
Notice of Opposition (Danisco US Inc.) to European Patent No. 3131912, dated Oct. 21, 2020.
Notice of Opposition (FrieslandCampina Nederland B.V.) to European Patent No. 3131912, dated Oct. 5, 2020.
Notice of Opposition (Greaves Brewster LLP) to European Patent No. 3131912, dated Oct. 21, 2020.
Notice of Opposition (Nestle Deutschland AG) to European Patent No. 2896628 dated Apr. 23, 2020.
Notice of Opposition (Nestle Deutschland AG) to European Patent No. 3131912 dated Feb. 24, 2020, 7 pages.
Notice of Opposition (Nestle Deutschland AG) to European Patent No. 3131912, Supplement, dated Apr. 23, 2020, 77 pages.
Notice of Opposition (Nestle Deutschland AG) to European Patent No. 3131912, Supplemental, dated Sep. 10, 2020.
Novel Foods Unit—2'-Fucosyllactose (2), European Minister of Health, No. 2017-08BNV, Dec. 19, 2017, 8 pages.
Novel Foods Unit—2'-Fucosyllactose (3), European Minister of Health, No. 2017-09BNV, Dec. 19, 2017, 8 pages.
Novel Foods Unit—2'-Fucosyllactose, European Minister of Health, No. 2016-03 BNV, Jun. 3, 2016, 37 pages.
Organo Corporation Product Sheet, Sugar Separation, 2018, 4 pages.
Proprietor's Response to the Notices of Opposition in EP2896628, dated Jan. 17, 2020, 21 pages.
Proprietor's Response to the Notices of Opposition in EP3131912, dated May 13, 2021, 46 pages.
Puritech Product Sheet, Fructose/Glucose, Jan. 16, 2021, 4 pages.
Puritech Product Sheet, Sugar Syrup Purification, Dec. 5, 2013, 2 pages.
Purolite Product Sheet, Chromatographic Separation Process in Corn Sweetener Refining, 2021, 6 pages.

* cited by examiner

PROCESS FOR EFFICIENT PURIFICATION OF NEUTRAL HUMAN MILK OLIGOSACCHARIDES (HMOS) FROM MICROBIAL FERMENTATION

CROSS-REFERENCE TO RELATED APPLICATIONS

This application is a continuation of U.S. patent application Ser. No. 16/277,731, filed 15 Feb. 2019, which is a continuation of U.S. patent application Ser. No. 15/112,724, filed 20 Jul. 2016 (now U.S. Pat. No. 10,377,787, issued on 13 Aug. 2019), which is a National Stage entry of International Application No. PCT/EP2014/079212, filed 23 Dec. 2014, which claims priority to European Patent Application No. 14151737.5, filed 20 Jan. 2014. The disclosures of the priority applications are incorporated in their entirety herein by reference.

The present application discloses a simple process for the purification of neutral human milk oligosaccharides (HMOs) produced by microbial fermentation. The process uses a combination of a cationic ion exchanger treatment, an anionic ion exchanger treatment, and a nanofiltration and/or electrodialysis step, which allows efficient purification of large quantities of neutral HMOs at high purity. Contrary to the purification currently used in fermentative production of neutral HMOs, the presented process allows the provision of HMOs without the need of a chromatographic separation. The so purified HMOs may be obtained in solid form by spray drying, as crystalline material or as sterile filtered concentrate. The provided HMOs are free of proteins and recombinant material originating from the used recombinant microbial strains and thus very well-suited for use in food, medical food and feed (e.g. pet food) applications.

Human milk represents a complex mixture of carbohydrates, fats, proteins, vitamins, minerals and trace elements. The by far most predominant fraction is represented by carbohydrates, which can be further divided into lactose and more complex oligosaccharides. Whereas lactose is used as an energy source, the complex oligosaccharides are not metabolized by the infant. The fraction of complex oligosaccharides accounts for up to $\frac{1}{10}$ of the total carbohydrate fraction and consists of probably more than 150 different oligosaccharides. The occurrence and concentration of these complex oligosaccharides are specific to humans and thus cannot be found in large quantities in the milk of other mammals, like for example domesticated dairy animals.

The existence of these complex oligosaccharides in human milk is known already for a long time and the physiological functions of these oligosaccharides were subject to medicinal research for many decades (Gura, T. (2014) Nature's first functional food. *Science* 345(6198) 747-749). For some of the more abundant human milk oligosaccharides, specific functions have already been identified (Bode, L. (2012) Human milk oligosaccharides: every baby needs a sugar mama. *Glycobiology* 22(9), 1147-1162; Bode L, Jantscher-Krenn E (2012) Structure-function relationships of human milk oligosaccharides. *Adv Nutr* 3(3) 3835-39:15; Morrow A L, Ruiz-Palacios G M, Altaye M, Jiang X, Guerrero M L, Meinzen-Derr J K, Farkas T, Chaturvedi P, Pickering L K, Newburg DS (2004) Human milk oligosaccharides are associated with protection against diarrhea in breast-fed infants. *J Pediatr* 145(3) 297-303).

The limited supply and difficulties of obtaining pure fractions of individual human milk oligosaccharides lead to the development of chemical routes to some of these complex molecules. However, synthesis of human milk oligosaccharides by chemical synthesis, enzymatic synthesis or fermentation proofed to be challenging. At least large-scale quantities as well as qualities sufficient for food applications cannot be provided until today. In this regard, particularly chemical synthetic routes to human milk oligosaccharides (e.g. fucosyllactose; see WO 2010/115935 A1) involve several noxious chemicals, which impose the risk to contaminate the final product.

Due to the challenges involved in the chemical synthesis of human milk oligosaccharides, several enzymatic methods and fermentative approaches were developed (Miyazaki et al., (2010) *Methods in Enzymol.* 480, 511-524; Murata et al., (1999) *Glycoconj. J.* 16, 189-195; Baumgartner, F. et al., (2013) Microb. Cell Fact. 12, 40; Lee et al., (2012) *Microb. Cell Fact.* 11, 48; U5 7,521,212 B1 or Albermann et al., (2001) Carbohydr. Res. 334(2) p 97-103). However, these methods—yield complex mixtures of oligosaccharides i.e. the desired product is contaminated with starting material such as lactose, biosynthetic intermediates and substrates such as individual monosaccharides and polypeptides etc.

Processes in the state of the art for purifying individual oligosaccharide products from these complex mixtures are technically complex and also uneconomical for food applications. For the purification of the disaccharides lactose or sucrose from complex mixtures such as whey or molasses, industrial scale processes have been developed which involve multiple crystallizations. The disadvantage of said methods is that they are elaborate and only lead to low yields.

For the purification of complex oligosaccharides from microbial fermentation, such as certain human milk oligosaccharides, gel-filtration chromatography is the method of choice until now. The disadvantage of gel-filtration chromatography is that it cannot be efficiently scaled up and it is unsuitable for continuous operation, Thus, gel-filtration chromatography is not economical and renders it impossible to provide certain human milk oligosaccharides—like 2'-fucosyllactose or lacto-N-tetraose—in reasonably amounts and quality to use them in human food or other applications such as animal food (e.g. pet food). The application as animal feed or pet food is interesting on the basis that also other mammals contain the same or similar neutral complex oligosaccharides in their milk as humans (e.g. 2'-fucosyllactose is also found in the milk of dogs, pigs, chimpanzee) (Castanys-Munzo, E., Martin, J. M & Prieto, P. A. (2013) 2'-fucosyllactose: an abundant, genetically determined soluble glycan present in human milk. *Nutr. Rev.* 71(12) 773-789).

Another problem is presented by the use of recombinant strains (recombinant bacterial or yeast strains) in the microbial fermentation, resulting in the contamination of the fermentation product with recombinant material. However, contamination with recombinant DNA or proteins is not acceptable by regulators and consumers today. Detection limits in particular for recombinant DNA molecules are very low. In case qPCR based detection is used, which is currently regarded as the gold standard for detection, even as little a single DNA molecules can be detected. Proteins in addition pose the risk of allergic reactions and should therefore be efficiently removed from the desired oligosaccharide product.

Electrodialysis (ED) represents a technique combining dialysis and electrolysis and can be used for the separation or concentration of ions in solutions based on their selective electronmigration through semipermeable membranes. First industrial applications of electrodialysis dated back into the early 1960 with the demineralization of cheese whey for the use in infant formula. Further developed applications of electrodialysis include the adjustment of pH of beverages such as wines, grape must, apple juice and orange juice.

The desalination for brackish water for the production of drinking water and the demineralization of milk whey for infant food production represent the largest area of application, today.

The basic electrodialysis principle consists of an electrolytic cell composed of a pair of electrodes submerged into an electrolyte for conduction of ions connected to a direct current generator. The electrode connected to the positive pole of the direct current generator is the anode, and the electrode connected to the negative pole is called cathode. The electrolyte solution then supports the current flow, which results from the movement of negative and positive charge ions towards the anode and cathode respectively. The membranes employed in the electrodialysis are essentially sheets of porous ion-exchange resins, owing negative or positive charge groups and therefore addressed as cationic or anionic membrane, respectively. The ion exchanger membranes are usually made of polystyrene carrying a suitable functional group (such as sulfonic acid or a quaternary ammonium group for cationic or anionic membranes, respectively) cross-linked with divinyilbenzene. As electrolyte, sodium chloride, or sodium acetate, sodium propionate etc. can be employed. The electodialysis stack is then assembled in such a way that the anionic and cationic membranes are parallel as in a filter press between two electrode blocks that the stream undergoing ion depletion is well separated from the stream undergoing ion enrichment (the two solutions are also referred to as diluate (undergoing ion depletion) and concentrate (undergoing ion enrichment). The heart of electrodialysis process is the membrane stack, which consists of several anion and cation-exchange membranes separated by spacers, and installed between two electrodes. By applying a direct electric current, anions and cations will migrate across the membranes towards the electrodes generating a diluate (desalted) and a concentrate stream.

Generally, the pore size of the employed membranes is rather small in order to prevent diffusion of the product from the diluate into the concentrate stream, driven by the often high concentration differences between the two streams. After separation from biomass, proteins and in particular recombinant DNA molecules (in the size of entire genomes) have to be removed quantitatively from the desired product. If at all possible the electrodialysis of such large molecules (in comparison to the molecular size of HMOs) would be rather lengthy and surely accompanied with significant losses of the desired product from the diluate into the concentrate.

Diafiltration is a process that involves the addition of fresh water to a solution in order to "wash out" or remove membrane permeable components. Thus, diafiltration can be used to separate components on the basis of their molecular size by using appropriate membranes, wherein one or more species are efficiently retained and other species are membrane permeable. In particular, diafiltration by using a nanofiltration membrane is effective for the separation of low molecular compounds from salts. In general, nanofiltration membranes possess a molecular weight cut-off in the range of 150 to 300 Daltons. Today, nanofiltration (NF) is widely used in the dairy industry for the concentration and demineralization of whey. Nanofiltration has already been employed for the enrichment of a human milk oligosaccharide fraction form human milk. In this approach, nanofiltration has been used in combination with enzymatic degradation of lactose to separate the HMO fraction from the milk lactose (Sarney D. B, Hale, C., Frankel, G & Vulfson, E. N. (2000) A novel approach to the recovery of biological active oligosaccharides from milk using a combination of enzymatic treatment and nanofiltration. *Biotechnol. Bioeng* 69, 461-467.

In the developed process for the efficient purification of food-grade human milk oligosaccharides from microbial fermentation, nanofiltration is employed in order to concentrate the desired product and also to remove membrane permeable salts.

Starting from this prior art, the technical problem is the provision of a novel process to provide neutral HMOs in high amounts, high purity and excellent yields.

The technical problem is solved by the process according to claim 1, the human milk oligosaccharide (HMO) according to claim 15 and the use of the HMO according to claim 19. The dependent claims display advantageous embodiments.

The present invention provides a process for purification of neutral human milk oligosaccharides (HMO) in a batch manner or in a continuous manner from a fermentation broth obtained by microbial fermentation wherein a purified solution comprising a neutral HMO at a purity of ≥80% is provided. The fermentation broth contains the neutral HMO, biomass, medium components and contaminants. The purity of the neutral HMO in the fermentation broth is <80%.

During the process the fermentation broth is applied to the following purification steps:
i) Separation of biomass from the fermentation broth,
ii) Cationic ion exchanger treatment for the removal of positively charged material,
iii) Anionic ion exchanger treatment for the removal of negatively charged material,
iv) Nanofiltration step (comprising or consisting of concentration and/or diafiltration of the neutral HMO) and/or electrodialysis step (especially for the removal of salts and other low molecular weight compounds).

Contaminants present in the cell-free fermentation broth are for example other oligosaccharides than the desired neutral HMO, like monovalent and divalent salts, amino acids, polypeptides, proteins, organic acids, nucleic acids, etc. The desired neutral HMO can be obtained at a purity of ≥80% in the purified solution.

The applicant has discovered that with the inventive purification process, an efficient purification of neutral HMOs from microbial fermentation can be attained, which delivers the HMO at purity suitable for food and feed applications. Furthermore the process is highly cost effective because no chromatographic separation step is needed. Furthermore, it has been discovered that the purity of ≥80% is achieved whether an electrodialysis step or a nanofiltration step is performed in step iv) or if both steps are performed in succession.

One advantage of the process according to the present is that the desired neutral HMOs are obtained free from DNA and proteins from the used recombinant microbial fermentation strain. Especially the implementation of a cationic ion exchanger treatment (step ii) allows the removal of positively charged material like e.g. positively charged proteins. Consequently, the inventive method provides an HMO which comprises less positively charged contaminant material compared to conventional purification schemes known in the prior art which do not implement a cationic exchanger treatment. It was further discovered that after passing the fermentation broth separated from the biomass (preferably by ultrafiltration) over a cationic ion exchanger (in proton form), the obtained solution was stable and could be stored at room temperature or under cooling for several weeks. Furthermore, the obtained neutral HMO is free of recombinant material, as judged by quantitative PCR with up to 50 amplification cycles. Moreover, the product obtained from the process according to the invention is characterized by low amounts or absence of proteins.

Furthermore, the neutral HMO purification according to the invention is highly efficient with yet unknown yields of >70% (optionally >75%) of the purified HMO (determined from cell free fermentation medium to HMO concentrate).

Thus, a hybrid process is provided comprising the steps of separation of biomass, ion exchanger, and a step of nanofiltration and/or electrodialysis, and preferably further comprising an activated carbon treatment, for the efficient provision of neutral HMOs at high purity free of recombinant genetic material, endotoxins and proteins form fermentation processes using recombinant fermentation strains. With the process according to the invention, large amounts of high quality human milk oligosaccharides may be provided in a very convenient and economical way.

The neutral HMO may be purified from a fermentation broth obtained by microbial fermentation using a recombinant microorganism, preferably bacteria or yeast, more preferably a recombinant microorganism grown in a chemically defined medium. Optionally, the biomass separated in step i) is recycled to the microbial fermentation.

In another preferred embodiment of the process according to the invention, the purity of the neutral in the fermentation broth is ≤70%, ≤60%, ≤50%, ≤40%, ≤30%, ≤20%, ≤10% or ≤5% and/or the purified solution contains the neutral HMO at a purity of ≥85%, preferably of ≥90%.

In another preferred embodiment of the process according to the invention, the yield of the neutral HMO is >70% (optionally >75%) and/or the purified solution is free of DNA, proteins, and/or recombinant genetic material.

In another preferred embodiment of the process according to the invention, the neutral HMO is selected from the group consisting of 2'-fucosyllactose, 3-fucosyllactose, 2',3-difucosyllactose, lacto-N-triose II, lacto-N-tetraose, lacto-N-neotetraose, lacto-N-fucopentaose I, lacto-N-neofucopentaose, lacto-N-fucopentaose II, lacto-N-fucopentaose III, lacto-N-fucopentaose V, lacto-N-neofucopentaose V, lacto-N-difucohexaose I, lacto-N-difucohexaose II, 6'-galactosyllactose, 3'-galactosyllactose, lacto-N-hexaose and lacto-N-neohexaose.

In a particularly preferred embodiment of the process according to the invention, the neutral HMO is 2'-fucosyllactose.

In another preferred embodiment of the process according to the invention, the separation of biomass from the fermentation broth is achieved by
a) ultrafiltration, preferably by separating biomass and materials >500 kDa, more preferably >150 kDa; and/or
b) filtration through a cross-flow filter, preferably with a cut-off ≤100 kDa, more preferably with a cut-off ≤10 kDa, even more preferably a cut-off ≤5 kDa;
wherein step a) is preferably implemented before step b).

In another preferred embodiment of the process according to the invention, at least one of the purification steps ii) to v) of the inventive process is repeated at least one time during the process.

In another preferred embodiment of the process according to the invention, the fermentation broth is applied at least one time to an activated carbon treatment after at least one of the purification steps i) to iv) for the adsorption of colour giving material and larger oligosaccharides to activated carbon. By applying the fermentation broth to this additional purification step, colour giving material and larger oligosaccharides can be removed from the fermentation broth.

The inventive process may be characterized in that
a) after at least one of the purification steps i) to iv); or
b) after at least one activated carbon treatment for the adsorption of colour giving material and larger oligosaccharides to activated carbon; or
c) before a concentration step which is implemented after at least one of the purification steps i) to iv);
the solution comprising the neutral human milk oligosaccharide is diafiltered and/or concentrated, Preferably, said solution is diafiltered and/or concentrated with a nanofiltration membrane, more preferably with a nanofiltration membrane having a size exclusion limit of ≤20 Å. Most preferably, the solution is diafiltered until a conductivity of ≤15 mS/cm, preferably ≤10 mS/cm, more preferably ≤5 mS/cm, is reached.

Diafiltration using nanofiltration was found efficient as a pretreatment to remove significant amounts of contaminants prior to an electodialysis treatment of the HMO containing solution. In addition, nanofiltration was also found to be efficient in the removal of low molecular contaminants after an ultrafiltration step, wherein said removal is beneficial for concentrating and demineralizing, the HMO solution prior to ion-exchanger treatment. The use of nanofiltration membranes for concentration and diafiltration in the purification of human milk oligosaccharides results in lower energy and processing cost, as well as in improved product quality, due to reduced thermal exposure, leading to reduced Maillard reactions and aldol reactions.

In a step before step i), a glucosidase treatment, preferably a β-glucosidase treatment, may be performed with the fermentation broth, wherein said treatment is preferably performed by
a) adding a microorganism strain capable of expressing one or more glycosidase enzyme(s) which are suitable for the degradation of unwanted intermediates, substrates and/or oligosaccharide side products; and/or
b) using a fermentation strain that expresses one or more glycosidase enzymes(s), preferably by adding an inducer to the fermentation broth and/or by shifting the temperature of the fermentation broth; and/or
c) adding one or more glycosidase(s), preferably at least a β-glucosidase, to the fermentation broth as a crude enzyme or as a purified enzyme.

In another preferred embodiment of the process according to the invention, the fermentation broth is concentrated after at least one of the purification steps i) to iv), preferably after purification step iv), using vacuum evaporation or reverse osmosis or nanofiltration (e.g. nanofiltration with a nanofiltration membrane having a size exclusion limit of ≤20 Å)
a) to a concentration of ≥100 g/L, preferably ≥200 g/L, more preferably ≥300 g/L; and/or
b) at a temperature of <80° C., preferably <50° C., more preferably 20° C. to 50° C., even more preferably 30° C. to 45° C., most preferably 35° C. to 45° C. (specifically relevant for vacuum evaporation or reverse osmosis); and/or
c) at a temperature of <80° C., preferably <50° C., more preferably 4° C. to 40° C. (specifically relevant for nanofiltration).

In another preferred embodiment of the process according to the invention, the purified solution is sterile filtered and/or subjected to endotoxin removal, preferably by filtration of the purified solution through a 3 kDa filter.

In another preferred embodiment of the process according to the invention, the neutral HMO containing solution is subjected to electrodialysis in order to further remove charged materials such as mono- and divalent salts.

In another preferred embodiment of the process according to the invention, the purified solution is concentrated to a concentration of >1.5 M and cooled to a temperature <25°, more preferable <8° C., to obtain crystalline material of the neutral HMO.

In another preferred embodiment of the process according to the invention, the purified solution is spray-dried, particularly spray-dried at a concentration of the neutral HMO of 20-50 (w/v), preferably 30-50 (w/v), more preferably 3.5-45 (w/v), a nozzle temperature of 110-150° C., preferably 120-140° C., more preferably 125-135° C. and/or an outlet temperature of 60-80° C., preferably 65-70° C.

Furthermore, the present invention includes a neutral human milk oligosaccharide (HMO) that is producible with the process according to the invention.

In a preferred embodiment, the HMO is present in a sterile filtered concentrate, e.g. sterile concentrate containing neutral HMO product with a concentration of ≥30% (w/v), more preferably ≥40% (w/v).

In another preferred embodiment, the HMO is spray-dried or crystallized.

In another preferred embodiment, the HMO is selected from the group consisting of 2'-fucosyllactose, 3-fucosyllactose, 2',3-difucosyllactose, lacto-N-triose II, lacto-N-tetraose, lacto-N-neotetraose, lacto-N-fucopentaose I, lacto-N-neofucopentaose, lacto-N-fucopentaose II, lacto-N-fucopentaose III, lacto-N-fucopentaose V, lacto-N-neofucopentaose V, lacto-N-difucohexaose I, lacto-N-difucohexaose II, 6'-galactosyllactose, 3'-galactosyllactose, lacto-N-hexaose and lacto-N-neonexaose.

In a particularly preferred embodiment, the HMO is 2'-fucosyllactose.

In another preferred embodiment, the HMO has
a) a conductivity of less than 1 mSi/cm at a 300 g/l solution;
b) is free of recombinant DNA material, optionally free of any DNA; and/or
c) is free of proteins derived from the recombinant microorganism, optionally free of any proteins.

Another preferred embodiment is directed to an HMO for use in medicine, preferably for use in prophylaxis or therapy of a gastrointestinal disorder.

Furthermore, the present invention includes the use of an HMO according to the invention as additive in food, preferably as additive in human food and/or pet food, more preferably as additive in human baby food.

The subject according to the application is intended to be explained in more detail with reference to the subsequent figures and examples without wishing to restrict said subject to the special embodiments.

EXAMPLE 1

Figure 1:
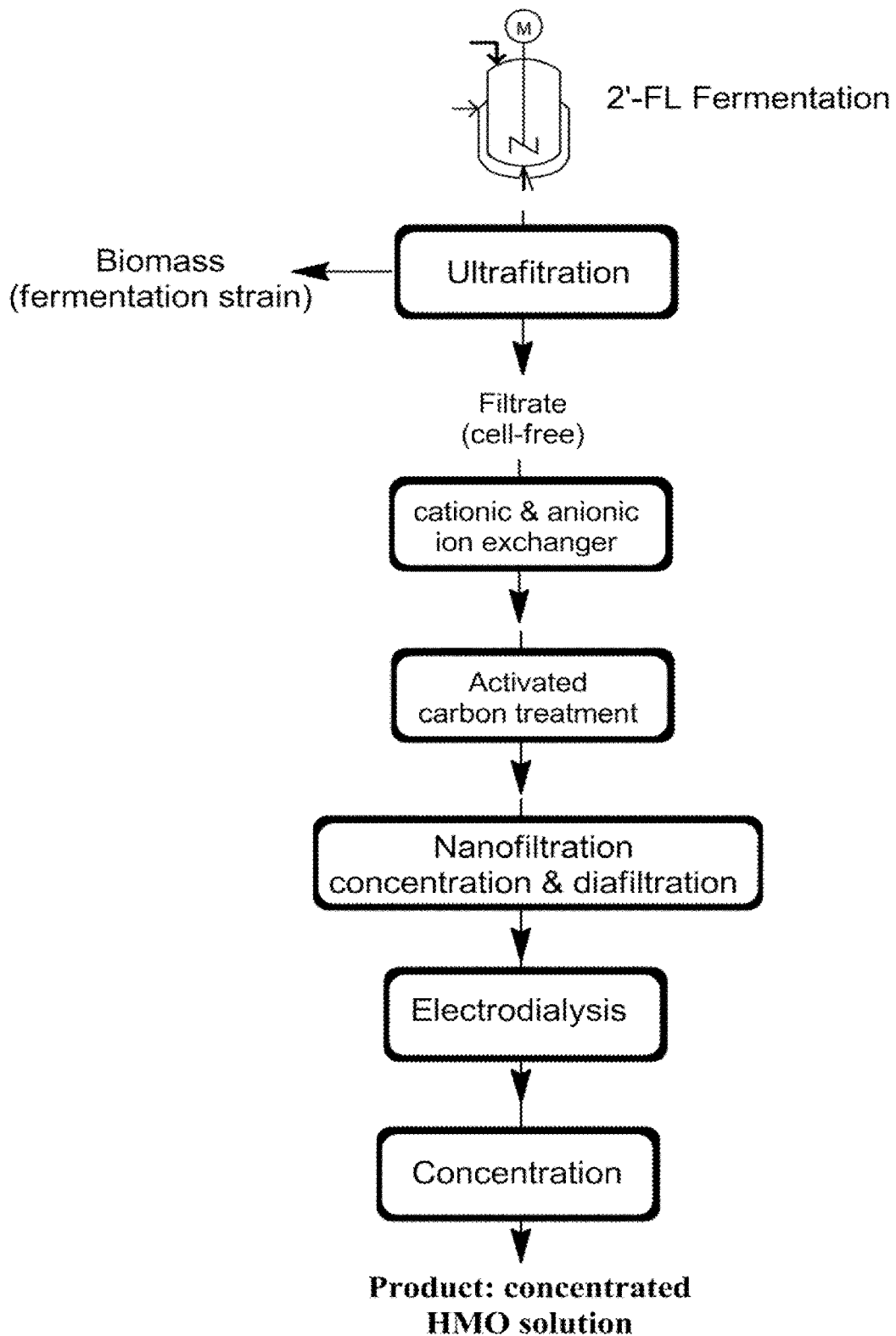
FIG. 1 shows a scheme of a preferred embodiment of the process according to the present invention for the purification of 2'-fucosyllactose from a fermentation broth comprising the steps: ultrafiltration, cationic and anionic ion exchanger treatment, activated carbon treatment, nanofiltration, electrodialysis and concentration.
Figure 2:
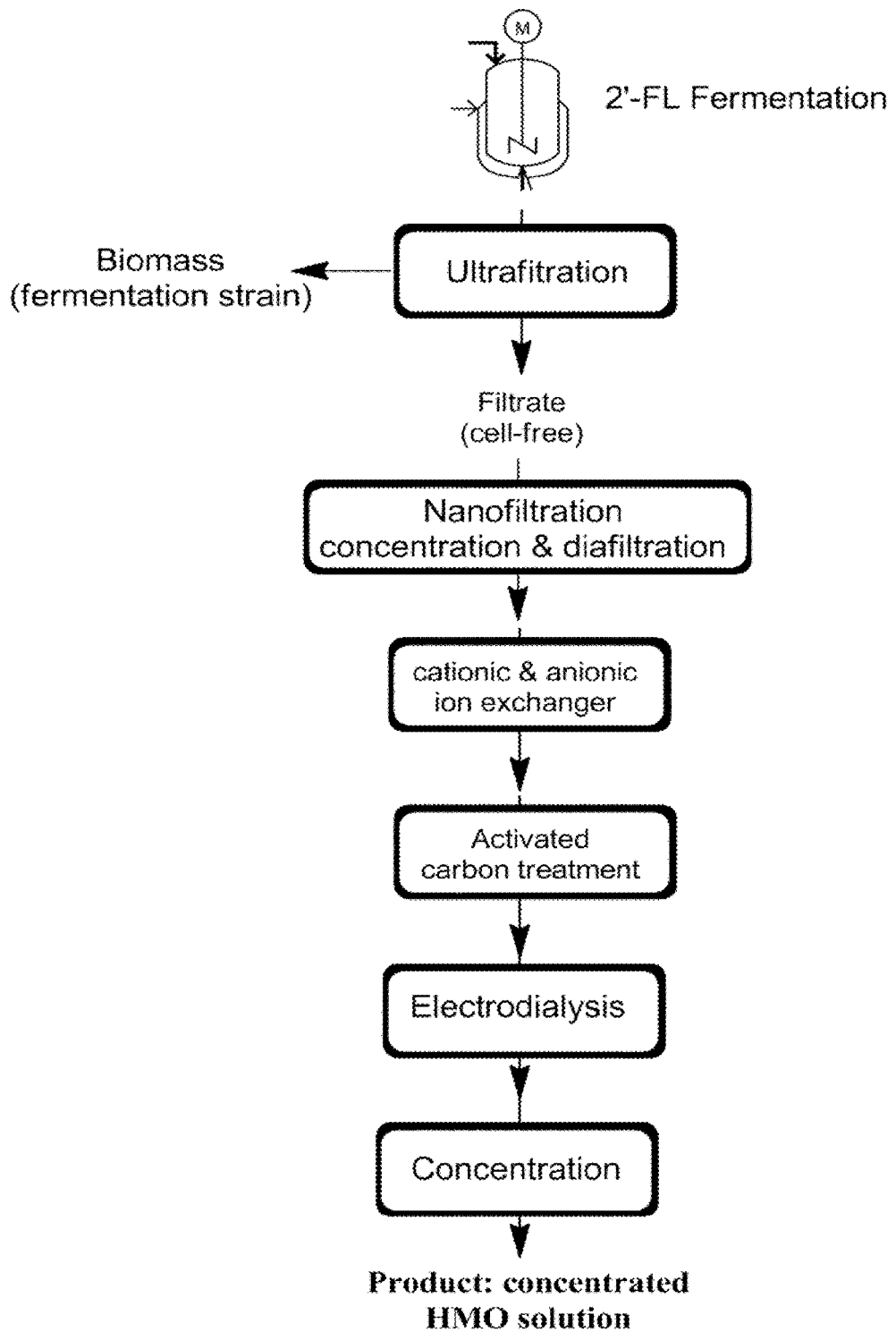
FIG. 2 shows a scheme of another preferred embodiment of the process according to the present invention for the purification of 2'-fucosyllactose from a fermentation broth comprising the steps: ultrafiltration, nanofiltration, cationic and anionic ion exchanger treatment, activated carbon treatment, electrodialysis and concentration.
Figure 3:
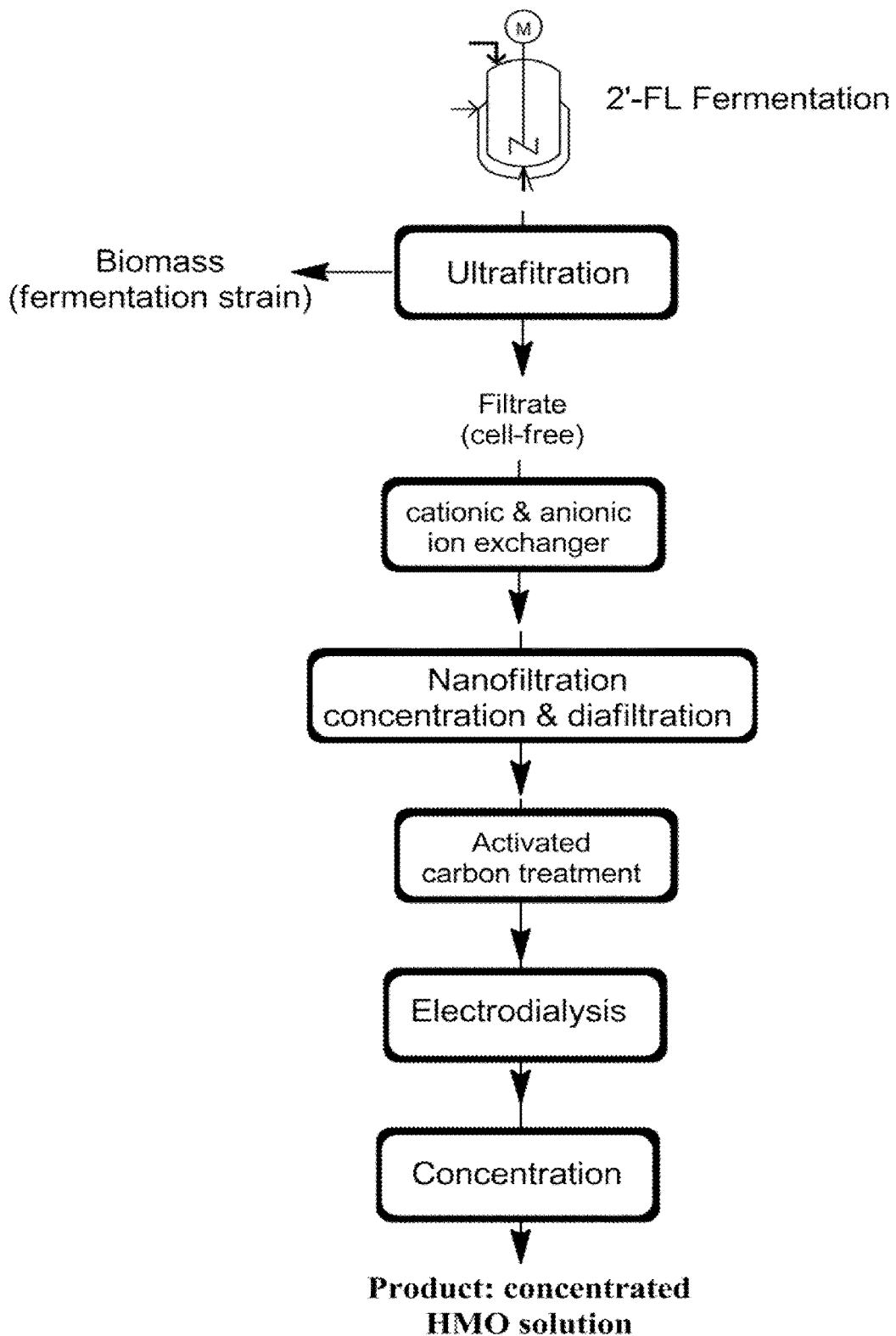
FIG. 3 shows a scheme of another preferred embodiment of the process according to the present invention for the purification of 2'-fucosyllactose from a fermentation broth comprising the steps: ultrafiltration, cationic and anionic ion exchanger treatment, nanofiltration, activated carbon treatment, electrodialysis and concentration.

Purification of 2'-fucosyllactose From Fermentation Using a Recombinant Microbial Production Strain I A 2'-fucosyllactose feed-batch fermentation employing a recombinant 2'-fucosyllactose synthesizing *E. coli* strain (*E. coil* BL21(DE3) ΔlacZ), containing a genomic integration 2'-fuosyltranferase, encoded by the wbgL gene (see EP 11 1151 571.4), and having an additional copy of the *E. coli* lacY, manB, manC, gmd and fcl all under the control of a strong constitutive tetracyclin promoter, containing a functional gal operon comprising the genes galM, galK, galT and galE, was grown in a defined salt medium. The defined salt medium comprised 7 g $l^{-1}$ NH$_4$H$_3$PO$_4$, 7 g $l^{-1}$ K$_2$HPO$_4$, 2 g $l^{-1}$ KOH, 0.37 g $l^{-1}$ citric acid, 1 ml $l^{-1}$ antifoam (Struktol J673, Schill+Seilacher), 1 mM CaCl$_2$, 4 mM MgSO$_4$, trace-elements and 2% glycerol as carbon source.

Trace elements consisted of 0.101 g $l^{-1}$ nitrilotriacetic acid, pH 6.5, 0.056 g $l^{-1}$ ammonium ferric citrate, 0.01 g $l^{-1}$ MnCl$_2$×4 H$_7$O, 0.002 g $l^{-1}$ CoCl$_2$×6 H$_2$O, 0.001 g $l^{-1}$ CuCl$_2$×2 H$_2$O, 0.002 g $l^{-1}$ boric acid, 0.009 g $l^{-1}$ ZnSO$_4$×7 H$_2$O, 0.001 g $l^{-1}$ Na$_2$MoO$_4$×2 H$_2$O, 0.002 g $l^{-1}$ Na$_2$SeO$_3$, 0.002 g $l^{-1}$ NiSO$_4$×6 H$_2$O.

Glycerol-feed consisted of glycerol 800 g $l^{-1}$ MgSO$_4$ 2.64 g $l^{-1}$ and trace element solution 4 ml $l^{-1}$. For 2'-fucosyllactose formation, a lactose feed of 216 g $l^{-1}$ was employed. The pH was controlled by using ammonia solution (25% v/v). Feed batch fermentation was cultured at 30° C. under constant aeration and agitation for 90 hours. At 90 hours after the start of the fermentation, most of the added lactose was converted into 2'-fucosyllactose, in order to remove lactose still present in the fermentation supernatant, a second bacterial strain was added to the fermentation vessel 90 hours after the fermentation start.

The added second bacterial strain was genetically identical to the first employed bacteria strain, differing, however, only in the expression of a genome integrated beta-galactosidase. Incubation of the added secondary bacterial strain resulted in the disappearance of the residual lactose within 5 hours. Approximately 10 ml starter culture of the second beta-galactosidase expressing bacterial strain was added per 1 l fermentation broth.

The biomass was then separated from the fermentation medium by ultrafiltration, using a cross-flow filter with a cut-off of 10 kDa (Microdyn Nardir).

An approximately 1 m$^3$ cell-free fermentation medium was obtained containing 42 g/l 2'-fucosyllactose. The cell-free fermentation medium was then passed over a strong cationic ion exchanger (Lewatit S 6368 A (Lanxess) in H$^+$ form, size of ion exchanger bed volume was 100 l), in order to remove positive charged contaminants. The obtained solution was then set to pH 7 by the addition of a 2 M sodium hydroxide solution.

The solution was then (without delay) passed over an anionic ion exchanger column (bed volume of ion exchanger was 100 l). The used strong anionic ion exchanger Lewatit S 2568 (Lanxess) was in chloride (Cl$^-$) form. The obtained solution was again neutralized to pH 7. The thus obtained solution was then diafiltrated using an Alfa-Laval NF99HF nanofiltration membrane and six volumes of sterile deionized water. The solution was further concentrated using the nanofiltration membrane wherein a 2'-fucosyllactose solution of 200 g/l and a conductivity of 7 mS/cm was obtained.

The concentrated 2'-fucosyllactose solution was then treated with activated carbon in order to remove color giving material such as Maillard reaction products and aldol reaction products. As activated carbon 20 g Norit GAC EN per l concentrated 2'-fucosyllactose solution was used, yielding a significantly decolorized solution.

The thus obtained concentrated 2'-fucosyllactose solution was then electrodialysed to 0.3 mS/cm using a PC-Cell BED 1-3 electrodialysis apparatus (PC-Cell, Heusweiler, Germany) equipped with PC-Cell E200 membrane stack. Said stack contained the following membranes: cation exchange membrane CEM: PC S K and the anion exchange membrane AEM:PcAcid60 having a size exclusion limit of 60 Da. A 0.025 M sulfamic acid (amidosulfonic acid) solution was used as an electrolyte in the ED process.

Then, the obtained solution was then concentrated under vacuum at 40° C. to obtain a 45% 2'-fucosyllactose solution. The concentrated solution was then again treated with ion exchangers, Lewatit S 5368 A (Lanxess) in $Na^+$ form (bed volume of the used ion exchanger was 10 l) and after neutralization with the anionic ion exchanger Lewatit S 2568 (Lanxess) in $Cl^-$ form (bed volume of the employed ion exchanger was 10 l).

The obtained 2'-fucosyllactose solution was then treated with activated carbon (Norit DX1 Ultra). For 1 l of a 45% 2'-fucosyllactose solution 30 g activated carbon were employed.

The solution was then again subjected to electrodialysis until a conductivity of less than 0.3 mSi/cm was obtained.

Subsequently, the solution was subjected to sterile filtration by passing the solution through a 3 kDa filter (Pall Microza ultrafiltration hollow fiber module SEP-2013, Pall Corporation, Dreieich).

Part of the obtained 2'-fucosyllactose solution was then spray dried for analysis.

For NMR spectra recording the spray-dried product was dissolved in hexadeuterodimethyl sulfoxide (DMSO-$d_6$). For the proton and $^{13}C$ analysis the following characteristic chemical shifts were observed:

$^1H$ NMR (500 MHz, DMSO-$d_6$) δ 6.63 (d, J=6.5 Hz, 1H), 6.28 (d, =4.7 Hz, 1H), 5.21 (d, J=2.4 Hz, 1H), 5.19 (d, J=2.4 Hz, 1H), 5.01 (d, J=2.2, 2H), 4.92 (d, J=5.0 Hz, 1H), 4.89 (dd, J=4.6, 1.3 Hz, 2H), 4.78 (d, J=5.3 Hz, 1H), 4.74 (d,J=5.1 Hz, 1H), 4.63 (m, 6H), 4.53 (t, d, J=5.5, 1H), 4.46 (d, J=5.2 Hz, 1H), 4.44 (d, J=5.0 Hz, 1H), 4.38-4.26 (m, 5H), 4.23 (d, J=0.9, 1H), 4.05 (d, J=0.9, 1H), 4.00 (quin, J=3.3, 1H), 3.68-3.50 (m, 7H), 3.59-3.50 (m, 13H), 3.50-3.37 (m, 6H), 3.24 (dt,=8.8, 2.2 Hz, 1H), 3.14 (m, 2H), 2.96 (td, J=8.4, 4.7 Hz, 1H), 1.04 (d, J=6.1 Hz, 3H), 1.03 (d, J=6.1 Hz, 3H).

$^{13}C$ NMR (126 MHz, DMSO-$d_6$) δ 100.99, 100.85, 100.35, 100.25, 96.59, 92.02, 78.13, 77.78, 77.16, 77.01, 75.27 75.05, 74.67, 73.70, 72.33, 71.62, 71.56, 70.91, 69.90, 69,64, 68.75, 68.16, 66.33, 60.17, 59.82, 59.67, 16.37, 16.36.

Chemicals shifts were found to be consistent with the 2'-fucosyllactose structure.

Using this protocol a 45% 2'-fucosyllactose concentrate with a purity of 94.5% could be obtained (determined by HPLC analysis). Major contaminants were 3'-fucosyllactose (1.8%), difucosyllactose (2.9%), and lactose (0.3%).

The yield of the purification was approximately 70%.

Importantly, no recombinant material could be determined in 10 g of freeze material using 50 cycles of OCR. Protein amount of the obtained material was determined as <50 μg/g freeze dried material by using a nano-Bradford assay (Roth, Karlsruhe Germany). Total amount of ash was determined with 0.19%. Concentration of heavy metals was (arsenic cadmium, lead and mercury) below 0.1 μg/g material. Endotoxin levels were determined to be <0.005 EU/ml 2'-fucosyllactose concentrate.

EXAMPLE 2

Purification of 2'-fucosyllactose From Fermentation Using a Recombinant Microbial Production Strain II A 1 $m^3$ microbial fermentation comprising 2'-fucosyllactose at a concentration of 47 g/L was filtered through a cross flow filter with a cut off of 100 kDa (Microdyn Nadir) to obtain a cell free fermentation medium.

As a fermentation medium the following medium was employed: Major medium components; glycerol 30 g/l, $NR_4H_2PO_4$ 7 g/l, $K_2HPO_4$ 7 g/l, citrate 0.3 g/l, KOH 2 g/l, $MgSO_4.7H_2O$ 2 g/l; trace elements: $CaCl_2.6H_2O$ 20 mg/l, nitrilotriacetic acid 101 mg/l, ammonium ferric citrate 56 mg/l, $MnCl_2.4H_2O$ 9.8 mg/l, $CoCl_2.6H_2O$ 1.6 mg/l, $CuCl_2.2H_2O$ 1 mg/l, $H_3BO_3$ 1.6 mg/l, $ZnSO_4.7H_2O$ 9 mg/l, $Na_2MoO_4.2H_2O$ 1.2 mg/l, $Na_2SeO_3$ 1.2 mg/l; feed substances; glycerol and lactose.

The cell free fermentation medium was then passed over a cationic ion exchanger (Lewatit S 6368 A (Lanxess) in $H^+$ form (volume of ion exchanger bed was 100 l) in order to remove positive charged contaminants. The obtained solution was then set to pH 7 by the addition of a 2 M sodium hydroxide solution. The solution was then, without delay passed over an anionic ion exchanger column (ion exchanger bed volume used was 100 l) comprising the strong anionic ion exchanger Lewatit S 2568 (Lanxess) in chloride ($Cl^-$) form. The obtained solution was again neutralized to pH 7. The so obtained solution was then diafitrated (using 10 volumes of sterile deionized water) and concentrated using a nanofiltration membrane (Alfa-Laval NF99HF) to obtain a 2'-fucosyllactose solution of 200 g/l and a conductivity of approx. 7 mSi/cm.

The concentrated 2'-fucosyllactose solution was then treated with activated carbon, using g Norit GAC EN per l concentrated 2'-fucosyllactose solution. To the filtered 2'-fucosyllactose solution 40 g/l Norit DX1 Ultra activated carbon was added. The solution was then exposed to the activated carbon at 4° C. for approximately 18 h. After 18 h, the activated carbon was removed from the 2'-fucosyllactose solution by filtration.

The solution was then electrodialysed to a conductivity of <0.3 mS/cm using a PC-Cell BED 1-3 electrodialysis apparatus (PC-Cell, Heusweiler, Germany) equipped with PC-Cell E200 membrane stack. Said stack contained the following membranes: cation exchange membrane CEM: PC SK and the anion exchange membrane AEM:PcAcid60 having a size exclusion limit of 60 Da. A 0.025 M sulfamic acid (amidosulfonic acid) solution was used as an electrolyte in the ED process.

The obtained solution was then concentrated to obtain a 40% 2'-fucosyllactose solution. The obtained 2'-fucosyllactose solution was then passed over a Lewatit S 2568 (Lanxess) $Cl^-$ form (bed volume 10 l) and treated with activated carbon (Norit DX1 Ultra) at 8° C. for 18 h. The solution was then subjected to sterile filtration by passing the solution through a 3 kDa filter (Pall Microza ultrafiltration hollow fiber module SEP-2013, Pall Corporation, Dreieich)

and spray-dried using a NUBILOSA LTC-GMP spray dryer (NUBILOSA, Konstanz, Germany).

Using this protocol, 2'-fucosyllactose with a purity of 94% could be obtained (determined by HPLC analysis). Major contaminants were 3'-fucosyllactose (1.8%), difucosyllactose (3.2%) and lactose (0.2%). The yield of the purification was approximately 70%.

The invention claimed is:

1. A process for the purification of a neutral human milk oligosaccharide in a batch manner or in a continuous manner from a fermentation broth obtained by microbial fermentation, wherein the neutral human milk oligosaccharide is selected from the group consisting of 3-fucosyllactose, 2',3-difucosyllactose, lacto-N-triose II, lacto-N-tetraose, lacto-N-neotetraose, lacto-N-fucopentaose I, lacto-N-neofucopentaose, lacto-N-fucopentaose II, lacto-N-fucopentaose III, lacto-N-fucopentaose V, lacto-N-neofucopentaose V, lacto-N-difucohexaose I, lacto-N-difucohexaose II, 6'-galactosyllactose, 3'-galactosyllactose, lacto-N-hexaose and lacto-N-neohexaose, which process comprises
   i) separating the microbial biomass from the fermentation broth;
   ii) subjecting the solution obtained in step i) to nanofiltration;
   iii) subjecting the separated fermentation broth obtained in step ii) to a cation exchanger or to an anion exchanger to obtain a solution;
   iv) subjecting the solution obtained in step iii) to the cation or anion exchanger not used in step iii);
   v) subjecting the solution obtained from step iv) to nanofiltration or reverse osmosis or vacuum evaporation or electrodialysis to obtain a purified solution of the neutral human milk oligosaccharide;
   vi) optionally treating the purified solution obtained after step iv) or step v) with activated carbon; and
   vii) spray-drying the purified solution obtained after step v) or vi), wherein the neutral human milk oligosaccharide in the purified solution obtained after step v) or after step vi), has a purity of ≥70% as determined by HPLC.

2. The process of claim 1, wherein the separating step i) is performed using ultrafiltration using a cross-flow filter.

3. The process of claim 1, wherein the separated fermentation broth obtained in step i) is diafiltrated before step ii).

4. The process of claim 1, further comprising adding a β-glucosidase to the fermentation broth prior to step i).

5. The process of claim 1, wherein step vi) treating the purified solution obtained after step iv) or step v) with activated carbon is performed.

* * * * *